(12) United States Patent
Mouchawar et al.

(10) Patent No.: US 7,139,604 B1
(45) Date of Patent: Nov. 21, 2006

(54) CARDIAC STIMULATION SYSTEM AND METHOD FOR DISCRIMINATING SINUS FROM NON-SINUS EVENTS

(75) Inventors: Nabil A. Mouchawar, Newhall, CA (US); Elia Arambula Mouchawar, Valencia, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 581 days.

(21) Appl. No.: 10/113,263

(22) Filed: Mar. 28, 2002

(51) Int. Cl.
*A61B 5/04* (2006.01)
(52) U.S. Cl. .................. 600/509; 600/515; 607/9; 607/14
(58) Field of Classification Search ............... 600/509, 600/515; 607/9, 13, 14
See application file for complete search history.

(56) References Cited

U.S. PATENT DOCUMENTS

| | | | |
|---|---|---|---|
| 4,510,945 A | 4/1985 | Barreras | 128/696 |
| 4,559,947 A | 12/1985 | Renger et al. | 128/419 PG |
| 4,788,980 A | 12/1988 | Mann et al. | 128/419 PG |
| 4,856,523 A | 8/1989 | Sholder et al. | 128/419 PG |
| 4,944,298 A | 7/1990 | Sholder | 128/419 PG |
| 5,103,822 A | 4/1992 | Duncan | 128/419 PG |
| 5,312,445 A | 5/1994 | Nappholz et al. | 607/9 |
| 5,507,783 A | 4/1996 | Buchanan | 607/14 |
| 5,772,691 A | 6/1998 | Routh et al. | 607/9 |
| 5,782,881 A | 7/1998 | Lu et al. | 607/9 |
| 5,810,739 A | 9/1998 | Bornzin et al. | 600/510 |
| 6,731,973 B1 * | 5/2004 | Voith | 600/513 |

* cited by examiner

*Primary Examiner*—Mark Bockelman

(57) ABSTRACT

A cardiac stimulation device and method discriminates sinus events from non-sinus events and provide a uniquely prescribed response upon detection of a specific event.

37 Claims, 6 Drawing Sheets

CARDIAC STIMULATION SYSTEM AND METHOD FOR DISCRIMINATING SINUS FROM NON-SINUS EVENTS

FIELD OF THE INVENTION

This invention relates generally to a programmable cardiac stimulating apparatus and a method for discriminating between various cardiac events, such as between sinus P-waves and non-sinus events sensed in the atria.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions. The normal heart rhythm arising from the sinus node is referred to as a sinus rhythm.

Disruption of the natural pacemaking and conduction system as a result of aging or disease can produce pathologic or non-sinus rhythms. Abnormal heart rhythms can be successfully treated by artificial cardiac pacing using implantable cardiac stimulation devices, including pacemakers and implantable defibrillators, which deliver rhythmic electrical pulses or anti-arrhythmia therapies to the heart at a desired pacing output (amplitude and pulse width) and rate.

A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

An electrical stimulus delivered to the heart causes the heart to contract when the patient's own intrinsic rhythm fails. To this end, cardiac stimulation devices include sensing circuits that sense the intracardiac electrogram and in particular sense the P-waves and/or R-waves of the intracardiac electrogram.

By monitoring the P-waves and/or R-waves, the sensing circuits of the stimulation device are able to determine the intrinsic rhythm of the heart. When the intrinsic rhythm falters, stimulation pulses can be provided as necessary to induce atrial and/or ventricular depolarizations at appropriate times in the cardiac cycle and thereby maintain a physiologically stable heart rhythm.

Single-chamber, dual-chamber and multi-chamber cardiac stimulation systems now exist. A single-chamber system stimulates and senses in one chamber of the heart (atrium or ventricle). A dual-chamber system stimulates and/or senses in both an atrial chamber and a ventricular chamber of the heart, and multi-chamber systems stimulate and/or sense in three or all four heart chambers.

Dual-chamber systems may be programmed to operate in one of a selection of operating modes. A three letter code (sometimes expanded to a five letter code) is used to describe the basic mode in which the device is operating. The three letter codes refer specifically to electrical stimulation for the treatment of bradycardia (a pathologically slow heart rate). A fourth position (when used) identifies the degree of programmability and rate modulation, and a fifth position (when used) refers to electrical stimulation therapy for the primary treatment of fast heart rhythms or tachycardias.

The first position of the operating code identifies the chamber to which the electrical stimulus is delivered. If the device is not capable of bradycardia support pacing, a "O" occupies this first position. If the device paces in the ventricle, this is indicated by a "V" in the first position; if the device paces in the atrium, this is identified as an "A". If stimuli can be delivered to both the atrium and the ventricle, the letter "D" is used to reflect dual-chamber stimulation.

The second position of the operating code identifies the chamber or chambers in which sensing occurs. Sensing is the ability of the pacemaker to recognize the intrinsic electrical activity of the heart, e.g., to sense P-waves and/or R-waves. The letters used in the second position are identical to those used in the first position.

The third position of the operating code identifies the way the pacemaker responds to a sensed signal. An "I" means that the stimulation output will be inhibited in response to a sensed intrinsic electrical signal. A "T" in the third position indicates an output stimulus will be triggered in response to a sensed intrinsic electrical signal. A "D" in the third position refers to both response modes.

A popular mode of operation for dual-chamber devices is the DDD mode. DDD systems have been developed to overcome the limitations of previous pacing methods. Specifically, DDD systems provide atrial pacing during atrial bradycardia, ventricular pacing during ventricular bradycardia, and atrial and ventricular pacing during combined atrial and ventricular bradycardia. In addition, DDD systems provide an atrial synchronous mode. Such features more closely approximate the normal response to exercise, or other physiological activity demanding a faster heart rate, by permitting a rate increase to occur commensurate with the rate of the sensed P-wave. This advantageously increases cardiac output and facilitates maintenance of AV synchrony.

In the DDD mode, a signal sensed on the atrial channel will inhibit the atrial output but trigger a ventricular output after a brief delay (the PV delay). If no atrial signal is sensed within a defined atrial escape interval, an atrial stimulation pulse will be delivered and will also trigger a ventricular output after a prescribed AV delay. If a native ventricular depolarization does not occur before the PV or AV delay expires, a ventricular stimulus will be released. If a native ventricular signal is sensed before the PV or AV delay expires, the ventricular output will be inhibited and other timers will be reset. If a native ventricular signal is sensed before the atrial stimulus is released, both the atrial and ventricular output pulses will be inhibited and the various timers will be reset.

The DDD mode possesses the characteristics of truer physiologic pacing because of the advantages in its hemodynamic and electrophysiologic abilities. The DDD mode of operation is designed to mimic the cardiac cycle electronically. Therefore, atrial or ventricular stimulation alone or atrial and ventricular stimulation in sequence will be delivered, so as to continuously maintain atrial and ventricular synchrony over a wide range of rates.

However, the DDD mode of operation can be ineffective in situations in which there is an instable atrial rhythm as evidenced by intermittent atrial flutter/fibrillation or frequent extra-systoles, or slow retrograde atrial activation that triggers ventricular pacing. DDD pacing is ineffective in providing atrial-ventricular synchronous pacing in these situations because the atrium cannot be stimulated, or atrial depolarization cannot be consistently sensed, or the timing of the atrial signal is inappropriate for governing physiological ventricular activation.

Besides these problems associated particularly with the DDD operating mode, there are other general problems with programmable cardiac stimulation devices associated with P-wave detection. Numerous signals may interfere with accurate detection of sinus P-waves. For example, a ventricular stimulation pulse may be sensed by the atrial sensing circuits and mislabeled as a P-wave. Such detection on one channel of the output from another channel is known as "cross talk."

Ectopic P-waves, which are P-waves arising from a location other than the sinus node, may also be detected and, undistinguished from sinus P-waves, trigger ventricular stimulation. Non-cardiac noise can also interfere with accurate sensing.

R-waves occurring in the ventricles may be of high enough amplitude to be sensed by the atrial sensing circuits. Known as far-field R-waves, these signals may also be misdetected as P-waves. In some patients, a depolarization in the ventricle may, at certain times, be conducted in a retrograde fashion back to the atria causing an atrial depolarization.

Detection of a retrograde depolarization or far-field R-wave as a sinus P-wave will trigger a ventricular stimulation output. If this cycle repeats itself, a pacemaker-mediated tachycardia, a highly undesirable situation, may be induced. Methods for preventing or terminating pacemaker-mediated tachycardia include modulation of the PV delay or the post-ventricular atrial blanking period.

Any of these events detected by the atrial sensing circuits can disrupt the physiological atrial-ventricular synchrony normally provided by DDD pacing or accurate atrial rate detection for the purposes of anti-tachycardia therapy delivery. Patients susceptible to atrial fibrillation may also be submitted to dynamic atrial overdrive pacing in which the atrium is paced at a rate higher than the intrinsic rate. This overdrive pacing acts to suppress the onset of atrial fibrillation. Inaccurate rate detection due to sensing of non-sinus events, however, could cause the atrium to be paced at a higher rate than necessary during dynamic atrial overdrive pacing. Therefore, various blanking schemes have been introduced that prevent detection of unwanted cross talk, far-field signals or retrograde P-waves. A post ventricular atrial blanking period (PVAB) is a period of absolute blanking of the atrial sensing circuit during the delivery of a ventricular stimulation pulse to prevent cross talk. A post-ventricular atrial refractory period (PVARP) is a relative refractory period during which signals may be sensed by the atrial sensing circuits but are generally presumed to be a far-field R-wave or a retrograde P-wave and are thus ignored and not used for tracking.

The disadvantage of using such blanking and refractory periods is that high atrial rates may go undetected when sinus P-waves do occur during a blanking or refractory interval. It is therefore desirable to accurately detect high atrial rates in order to provide appropriate corrective action. Known methods for responding to a high atrial rate include anti-tachycardia pacing and automatic device operating mode switching. By changing the operating mode from DDD to a single chamber mode, for example VVI, the high atrial rate is no longer tracked by the ventricular output.

It is desirable, therefore, to detect sinus P-waves and distinguish these signals from noise, ectopic P-waves (also known as premature atrial contractions), retrograde P-waves, or far-field R-waves. By accurately detecting and distinguishing sinus and non-sinus events sensed by the atrial sensing circuits, the stimulation device may respond appropriately in terms of ventricular tracking of the atrial rate, avoiding pacemaker-mediated tachycardia, delivering anti-tachycardia therapies, and executing atrial suppression algorithms.

In the ventricular channel, cross talk sensing occurs when the ventricular sensing circuits sense an atrial stimulation pulse. The atrial stimulation pulse is incorrectly detected as an intrinsic R-wave. The likelihood of cross talk occurring is increased when the programmed ventricular sensitivity is high or the atrial stimulation pulse amplitude is high. The undesirable consequence of cross talk sensing is the inhibition of a ventricular stimulation pulse when in fact ventricular pacing is needed.

One solution to cross talk sensing is the application of a ventricular blanking period, which is an absolute blanking period following an atrial stimulation pulse, combined with a "Ventricular Safety Standby" feature (VSS). This Ventricular Safety Standby (VSS) feature prevents inappropriate inhibition of the ventricular output when cross talk signal detection occurs. When Ventricular Safety Standby is enabled, a cross talk detection window begins immediately after the ventricular blanking interval terminates. The cross talk detection interval is set to a specified value minus the ventricular blanking interval. If the ventricular channel senses an event during the cross talk detection window, the event is presumed to be cross talk, and a ventricular stimulation pulse is delivered at a specified interval after the atrial pulse. If the AV interval is programmed to a value less than the specified value, the ventricular pulse is delivered at the end of the interval. Additionally, if a ventricular event is sensed after the cross talk window terminates, then the pending ventricular pulse is inhibited. While this feature ensures that the ventricle will be stimulated in situations of cross talk, discrimination between actual cross talk and true ventricular activity is not made.

For tracking pacing modes (such as DDD or DDT), not distinguishing between the presence of intrinsic ventricular activity and cross talk could lead to the delivery of a stimulation pulse during a T-wave, which can induce ventricular tachycardia in susceptible patients. By combining morphology discrimination with a method to characterize cross talk, the stimulation device can determine whether a sensed ventricular event is cross talk or a true intrinsic event and respond in the safest manner possible.

Thus, it is desirable, in a cardiac stimulation device, particularly in dual chamber or multichamber cardiac stimulation devices, to provide methods for clearly discriminating between cardiac sinus events and any other events that may be sensed including non-sinus events, cross talk, or far-field events. It is further desirable to provide a uniquely prescribed response to each of these identified events to ensure appropriate device function and the greatest level of safety for the patient.

SUMMARY OF THE INVENTION

The present invention addresses these needs by providing an implantable cardiac stimulation device capable of discriminating sinus P-waves or sinus R-waves from other events that may be detected by atrial or ventricular sensing circuitry including ectopic P-waves, far-field R-waves, retrograde P-waves, cross talk or noise. After specifically identifying a sensed event, prescribed actions are taken by the stimulation device such that the most appropriate and safest response to the detected event is provided.

Discrimination between sensed events is accomplished in one embodiment by measuring a characteristic of a sensed signal, such as peak amplitude, maximum slope, signal width, signal integral, or signal morphology, and comparing the measured signal characteristic to a reference signal characteristic for each of type of event to be identified. Upon detecting an approximate match between a sensed signal characteristic and a reference signal characteristic, the stimulation device provides an appropriate event response, which may include stimulation pulse delivery, inhibition of stimulation, device mode switching, or different responses for determination of atrial rate for atrial suppression or anti-tachycardia therapies.

The foregoing and other features of the present invention are realized by providing an implantable cardiac stimulation device equipped with cardiac data acquisition capabilities. A preferred embodiment of the stimulation device includes a control system for controlling the operation of the device; a set of leads for receiving cardiac signals and for delivering atrial and ventricular stimulation pulses; a set of sensing circuits comprised of sense amplifiers for sensing and amplifying the cardiac signals; and pulse generators for generating atrial and ventricular stimulation pulses.

In addition, the device includes memory for storing operational parameters for the control system, and storing data such as reference signal parameters or reference signal morphologies. The device is equipped with a data acquisition system for sampling sensed signals to allow for comparison of a sensed signal to reference signal parameters or morphologies such that the type of signal sensed may be determined. The device also includes a telemetry circuit for communicating with an external programmer.

When operating according to one embodiment, one or more reference values representing a characteristic sinus P-wave signal and a characteristic sinus R-wave signal, as well as any other signals to be specifically discriminated from sinus P-waves and R-waves, are acquired and stored in memory. Preferably, a reference signal morphology template is acquired and stored for each type of event to be detected. If an unknown complex is encountered, it could be stored for later classification by the physician.

Upon delivery of a ventricular stimulation pulse, a brief atrial blanking period is applied in the atrial sensing circuits followed first by a brief atrial refractory period and second by an atrial alert period. If an atrial signal is sensed during the atrial relative refractory period, or during the atrial alert period, a characteristic of the sensed signal is compared to the reference value for a sinus P-wave. If the sensed signal characteristic, preferably signal morphology, approximately equals a sinus P-wave reference value, the stimulation device takes a sinus P-wave response.

The response to a sinus P-wave detected during the atrial alert period will typically be to inhibit the atrial output and start a PV delay timer so that the P-wave is tracked for the purposes of ventricular stimulation. The response may also count the atrial event for atrial rate determination. If a sinus P-wave is detected during the atrial relative refractory period, the stimulation device detects a high atrial rate. In this case, a sinus P-wave response is taken for preventing high atrial rate tracking such as to ignore the P-wave for ventricular tracking purposes, or to trigger an automatic mode switch to a non-tracking ventricular stimulation mode. If the high atrial rate exceeds atrial tachycardia detection limits, anti-tachycardia therapy may be delivered.

If the sensed signal does not approximately equal a sinus P-wave reference value, it is considered a non-sinus event. The stimulation device takes a non-sinus event response that includes first identifying the event more specifically as a premature atrial contraction, a far-field R-wave or a retrograde P-wave by comparing the sensed signal to reference values for each of these events. If no match to these non-sinus events is recognized, the sensed event is identified as noise and stored for later reclassification by a physician. Once the non-sinus event is specifically identified, the stimulation device takes an appropriate response.

For example, during dual-chamber ventricular tracking modes, a non-sinus signal should not be tracked. The response to premature atrial contraction detection may be different than the response to sinus P-wave detection for purposes of atrial rate determination during dynamic atrial overdrive pacing. In the case of a far-field R-wave detection, the device response may include an action to deal with an over-sensed P-wave in the atrium. In case of far-field R-wave detection and retrograde P-wave detection, an action to suppress pacemaker-mediated tachycardia is preferably included in the device response. Furthermore, a retrograde P-wave or a far field R-wave is not counted for determination of atrial rate or atrial tachycardia detection. If the detected atrial signal does not approximately match any of the reference signals, the stimulation device takes a noise response, and can also be stored for later classification by a physician.

In the ventricular channel, a brief ventricular blanking period is applied in the ventricular sensing circuitry upon delivery of an atrial stimulation pulse followed by a cross talk detection window. A reference signal morphology representative of a sinus R-wave is used to discriminate between cross talk events and intrinsic R-waves sensed by the ventricular sensing circuitry during the cross talk detection window. Specific device actions may be taken in response to the detection of sinus R-waves and the detection of cross talk. In particular, a signal sensed during the cross talk detection window that is identified as an intrinsic R-wave will result in the inhibition of a ventricular stimulation pulse whereas detection of noise will not inhibit the ventricular stimulation pulse output.

Stimulation device performance is thus improved by the methods of the present invention because the device response to sensed events is based on confirmation of the specific type of event detected rather than assuming the nature of the event based only on timing and responding without confirmation of what the event actually is. Using the methods included in the present invention, the device will discriminate between retrograde, far-field, cross talk, noise and intrinsic events. The system and method of the present invention are then able to provide the most appropriate response. By accurately detecting and distinguishing sinus and non-sinus events, blanking and refractory periods can be minimized thus reducing the amount of time the stimulation device is blinded to intrinsic activity.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at improving cardiac stimulation device performance by providing methods for accurately distinguishing sinus P-waves from premature atrial contractions, far-field R-waves, retrograde P-waves, and noise in the atrial channel and distinguishing sinus R-waves from cross talk in the ventricular channel. By providing accurate atrial rate detection, pacemaker mediated tachycardia is more effectively prevented and the performance of dynamic atrial overdrive pacing and automatic mode switching algorithms are improved. By accurately distinguishing sinus R-waves from cross talk, the likelihood of ventricular safety standby pacing is not necessary, therefore saving battery energy.

A general cardiac stimulation device will be described in conjunction with FIGS. 1 and 2 in which features included the present invention could be implemented. It is recognized, however, that numerous variations of such a device exist in which the methods of the present invention could be implemented without deviating from the scope of the present invention.

Figure 1:
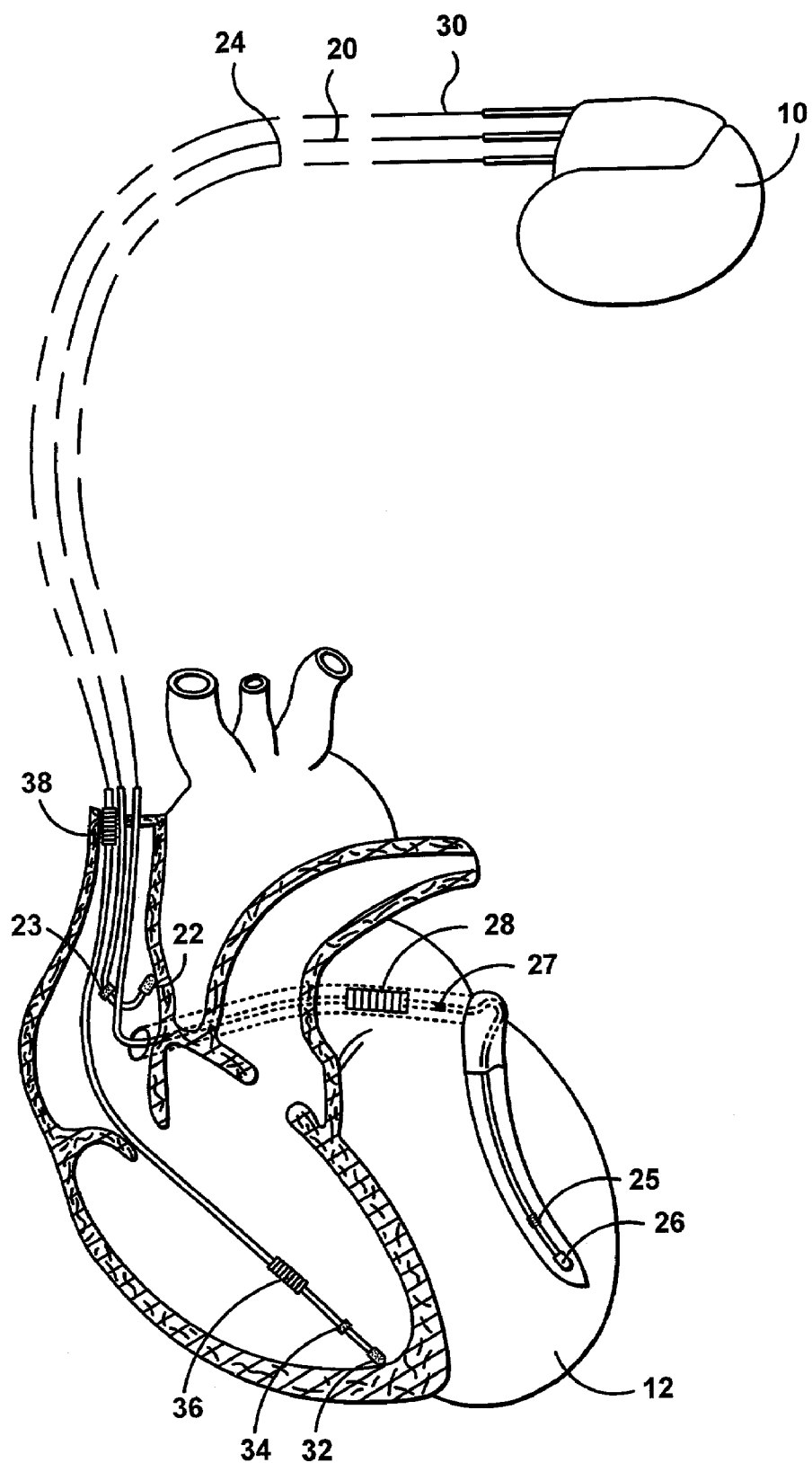
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to: receive atrial and ventricular cardiac signals; deliver left ventricular pacing therapy using at least a left ventricular tip electrode 26 for unipolar configurations or in combination with left ventricular ring electrode 25 for bipolar configurations; deliver left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
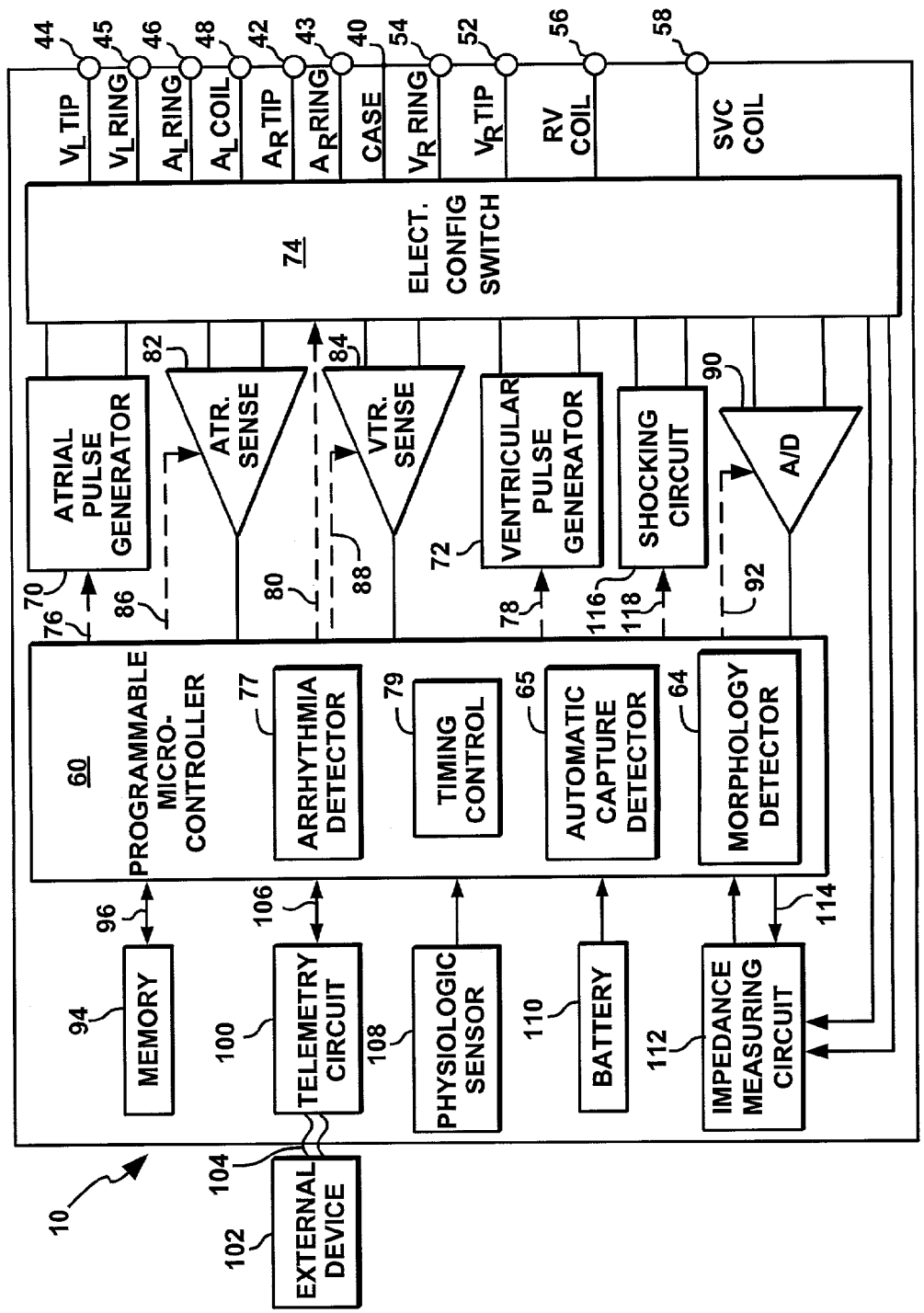
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. The stimulation device 10 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal (AR TIP) 42 adapted for connection to the atrial tip electrode 22. The connector may also include a right atrial ring terminal ($A_R$ RING) 43 for connection to the right atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interchamber (A—A) delay, or ventricular interchamber (V—V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to the step of confirming that the sensed electrical signal as the signal being sought by the detector. As an example, "detection" applies to the detection of both proper rhythms (i.e., "R wave" or "R wave") as well as improper dysrhythmias including arrhythmia and bradycardia (e.g., detection of the absence of a proper rhythm.)

The timing intervals between sensed events (e.g., P-waves, R-waves, and depolarization signals associated with fibrillation which are sometimes referred to as "F-waves" or "Fib-waves") are then classified by the arrhythmia detector 77 by comparing them to a predefined rate zone limit (e.g. bradycardia, normal, low rate ventricular tachycardia, high rate ventricular tachycardia, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". In the embodiment shown in FIG. 2, the microcontroller 60 includes an automatic capture detector 65 that searches for an evoked response signal following a stimulation pulse during a "detection window" set by timing control circuitry 79. The microcontroller 60 enables the data acquisition system 90 via control signal 92 to sample the cardiac signal that falls in the capture detection window. The sampled signal is evaluated by automatic capture detector 65 to determine if it is an evoked response signal based on its amplitude, peak slope, morphology or another signal feature or combination of features. The detection of an evoked response during the detection window indicates that capture has occurred.

In accordance with the present invention, data acquisition system 90 may be used to sample cardiac signals sensed by atrial sensing circuit 82 or ventricular sensing circuit 84 for the purpose of determining the type of signal, e.g., sinus P-wave, premature atrial contraction, retrograde P-wave, noise, etc., that has been sensed. Preferably, the sampled signal is compared to a reference signal morphology template by morphology detector 64, included in microcontroller 60, in order to confirm the type of signal sensed. Representative methods of the present invention for distinguishing between a number of sensed events occurring in the atria and between noise and sinus R-waves in the ventricles will be described in detail with reference to FIGS. 3 through 5.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 μA, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
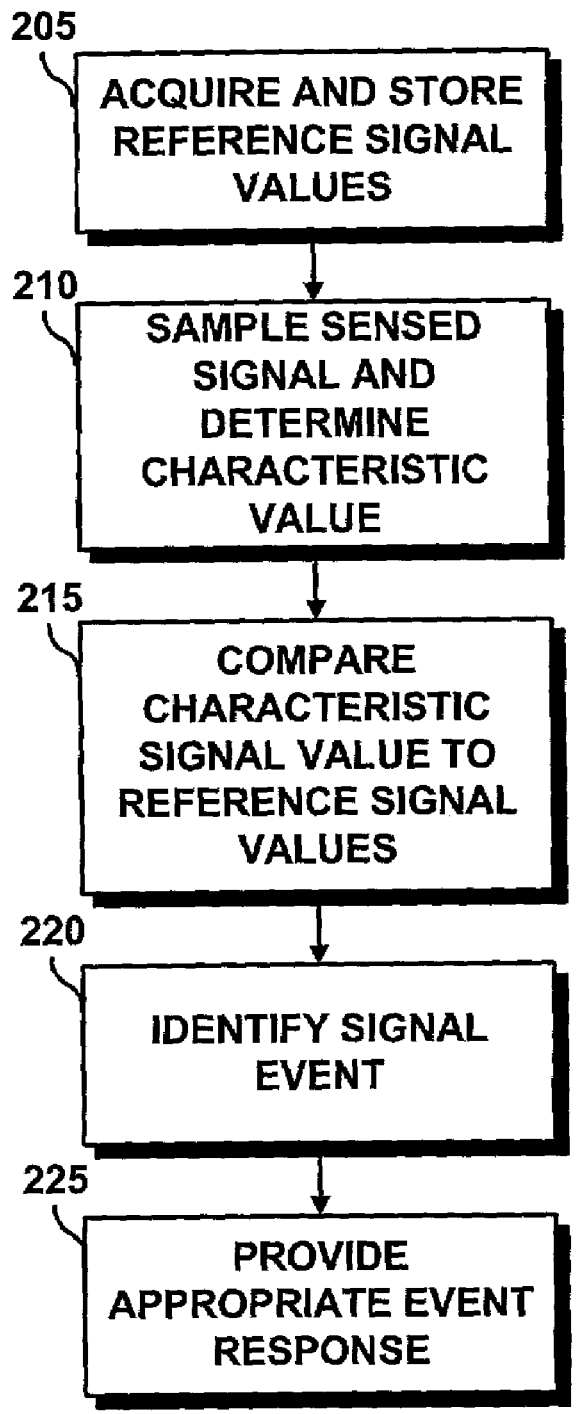
FIG. 3 is a flow chart describing an overview of the method implemented according to the present invention, for distinguishing sinus P-waves from other signals that may be sensed in the atria.

In FIG. 3, a flow chart is shown describing an overview of the operation and novel features implemented in one embodiment of the device 10 for discriminating between sinus and non-sinus events. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The first step 205 of the method 200 shown in FIG. 3 is to acquire and store a characteristic value of a reference signal corresponding to each type of event to be detected. Reference signal values preferably include a signal morphology, but may also be a peak amplitude, peak slope, signal integral, or a signal width. One or more of these reference values may be stored for later comparison to sensed signal characteristics for identifying sensed events. Reference signal values may be acquired and determined automatically or entered manually by a clinician.

During normal operation of the device 10, a signal sensed by atrial sensing circuit 82 or ventricular sensing circuit 84 is sampled by data acquisition system 90 at step 210, and the signal morphology (or another characteristic signal value) is determined by morphology detector 64. At step 215, a characteristic value of the sensed signal is compared to the reference signal values.

In the embodiment shown in FIG. 2, morphology detector 64 is used to compare the signal morphology of the sensed signal to the morphology of a reference signal. The sensed signal value is compared to each of the acquired event reference signals until an approximate match is found. The sensed signal is then identified as the event corresponding to the matching reference signal value at step 220. At step 225, device 10 provides an appropriate response to the identified event.

Figure 4:
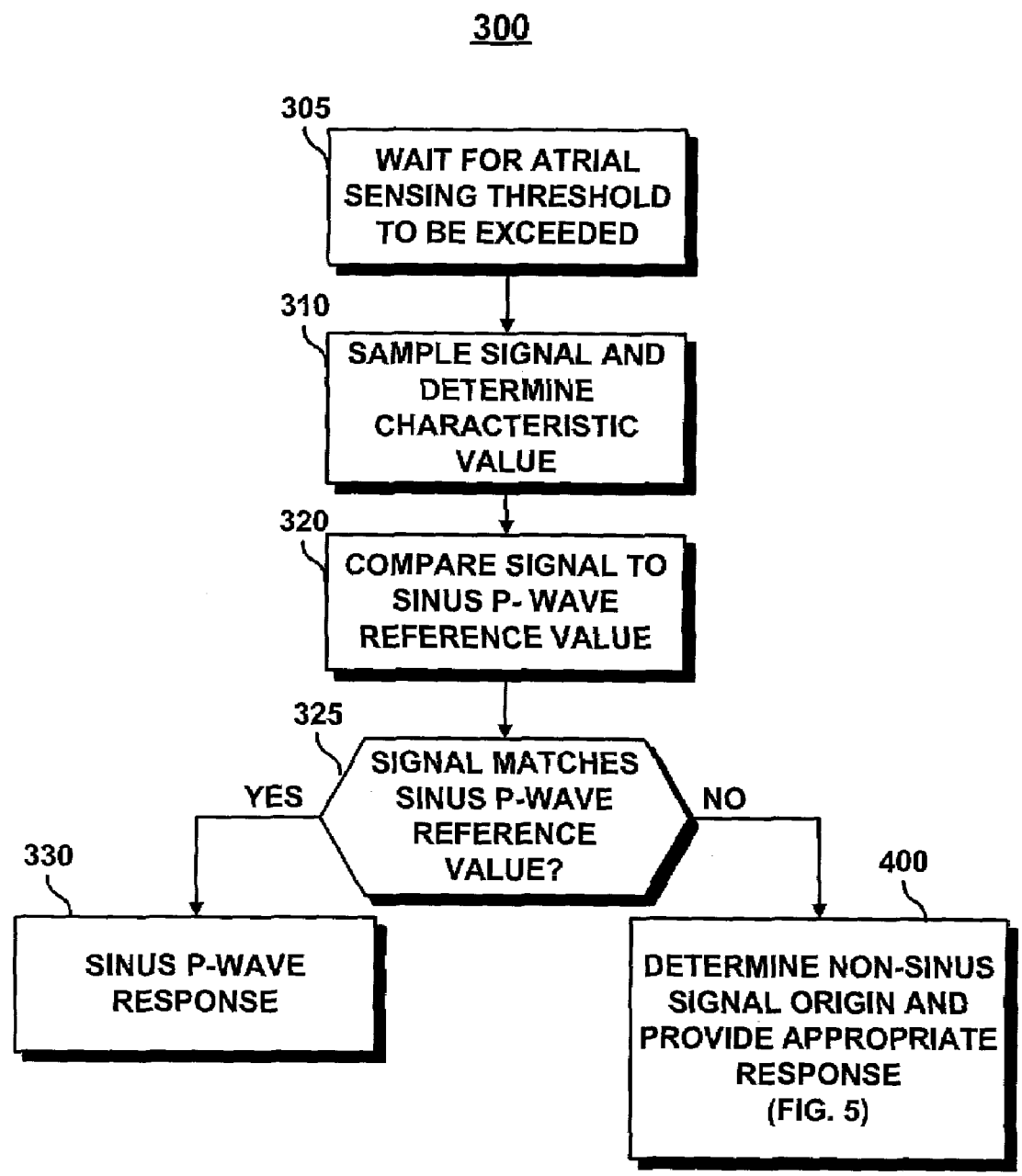
FIG. 4 is a flow chart depicting a method for determining the type of atrial signal sensed and providing an appropriate response to the sensed signal, to be implemented during the operation of FIG. 3.

The flow chart shown in FIG. 4 illustrates the operations of FIG. 3 as applied in the atrial channel for discriminating between sinus P-waves and other non-sinus events that may be detected by the atrial sensing circuit. At step 305, atrial sensing circuit 82 senses for events exceeding the atrial sensing threshold that occur during an atrial refractory period or during an atrial alert period, which successively follow a ventricular stimulation pulse. Once an atrial event is sensed, the signal is sampled by data acquisition system 90 and a characteristic value of the sampled signal is determined for comparison to previously acquired reference signal values.

At step 320, the characteristic value of the sampled signal is compared to the reference value for a sinus P-wave. If the characteristic value of the sampled signal approximately matches the sinus P-wave reference value, as determined at decision step 325, sinus P-wave detection is confirmed.

The stimulation device 10 responds accordingly at step 330 by executing a sinus P-wave response. An appropriate sinus P-wave response typically includes inhibition of a pending atrial stimulation pulse, tracking of the atrial P-wave for ventricular pacing, and counting the P-wave for determining the atrial rate for use by dynamic atrial overdrive or atrial tachycardia detection algorithms. If the sinus P-wave is detected during the atrial refractory period, it may be ignored for ventricular tracking purposes or may result in an automatic mode switch if the resulting atrial rate exceeds the maximum tracking rate.

If, at decision step 325, the sensed signal does not match the reference value for a sinus P-wave, method 300 calls upon a method 400 for specifically identifying the specific type of signal that has been sensed. Method 400 allows the device 10 to specifically confirm whether the sensed signal is an ectopic P-wave, a far-field R-wave, a retrograde P-wave or noise based on signal analysis rather than the timing of the sensed signal.

Conventionally, any event detected in the atrial refractory period is identified as a non-sinus P-wave and any event detected in the atrial alert period is considered to be a sinus P-wave. Any response of the stimulation device according to a time-based signal identification, made without confirmation of the true identity of the signal, may not be the ideal device response.

Figure 5:
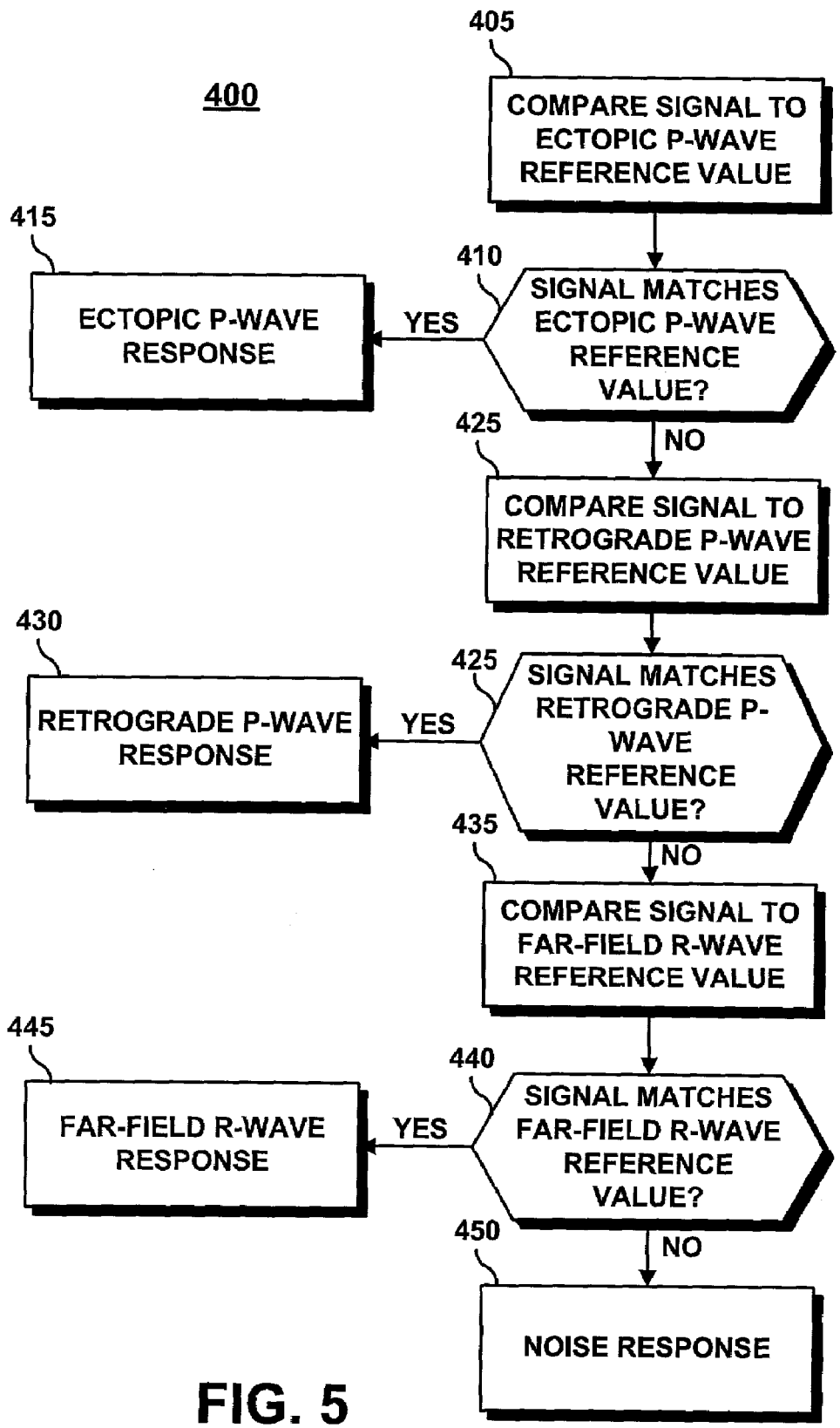
FIG. 5 is a flow chart depicting a method for sensing ventricular signals and distinguishing between sinus R-waves and noise, and for providing an appropriate response to the detected signal, according to the present invention.

In FIG. 5, a flow chart is shown providing an overview of the method 400 which further analyzes the sensed signal to determine specifically the event that the sensed signal represents, such that the most appropriate device response is provided. Beginning at step 405, method 400 compares the characteristic value of the sensed signal to a reference value for an ectopic P-wave. If the values are approximately equal or similar, as determined at decision step 410, stimulation device 10 provides an ectopic P-wave response at step 415.

A number of responses may be provided upon ectopic P-wave detection. During ventricular tracking, the stimulation device may ignore an ectopic P-wave in tracking ventricular stimulation to the atrial rate, or provide ventricular stimulation at a different PV interval than the PV interval following a sinus P-wave.

The stimulation device 10 may also provide a more aggressive dynamic atrial overdrive response to an ectopic P-wave since an ectopic P-wave may be a precursor to atrial tachycardia or fibrillation in some patients. In other patients, an ectopic P-wave may not be a precursor to atrial tachycardia or fibrillation and may therefore be ignored for the purposes of rate determination during dynamic atrial overdrive pacing. Hence, the response of device 10 to an ectopic P-wave detection may be programmable in one embodiment so that the response may be tailored according to individual patient need.

If the sensed signal is not confirmed to be an ectopic P-wave at step 410, the sensed signal is compared to the reference value for a retrograde P-wave at step 425. If the sensed signal approximately matches the retrograde P-wave reference value as determined at step 425, the stimulation device 10 provides a retrograde P-wave response at step 430.

A retrograde P-wave response preferably includes a pacemaker-mediated tachyarrhythmia avoidance response. Thus, during ventricular tracking, the retrograde P-wave is not used for tracking ventricular stimulation to the atrial rate. Furthermore, a retrograde P-wave is preferably not used for determining the atrial rate for the purposes of atrial tachycardia or fibrillation detection or for dynamic atrial overdrive pacing.

If a retrograde P-wave is not confirmed at decision step 425, the sensed signal is compared to the reference value for a far-field R-wave at step 435. If a characteristic value of the sensed signal approximately equals the far-field R-wave reference value as determined at decision step 440, the stimulation device 10 provides a far-field R-wave response at step 445. For example, a far-field R-wave detected on the atrial channel is not to be used for atrial rate determination for the purposes of detecting atrial tachycardia or fibrillation, nor used for ventricular tracking, or determining the atrial rate during dynamic atrial overdrive pacing. If desired, adjustments to some operating parameters could be made to avoid far-field R-wave sensing, such as reducing the atrial sensitivity or decreasing the ventricular stimulation amplitude. However, accurate recognition of a far-field R-wave allows the stimulation device 10 to avoid inappropriately responding to it as if it were a sinus P-wave.

If a far-field R-wave detection is not confirmed at decision step 440, the stimulation device 10 concludes that the sensed atrial signal is noise and responds accordingly at step 450. The response of device 10 to noise detection is preferably to ignore the noise signal for all operational purposes. It is also possible that the template of the unknown or unidentified signal be stored for later classification by the physician.

Figure 6:
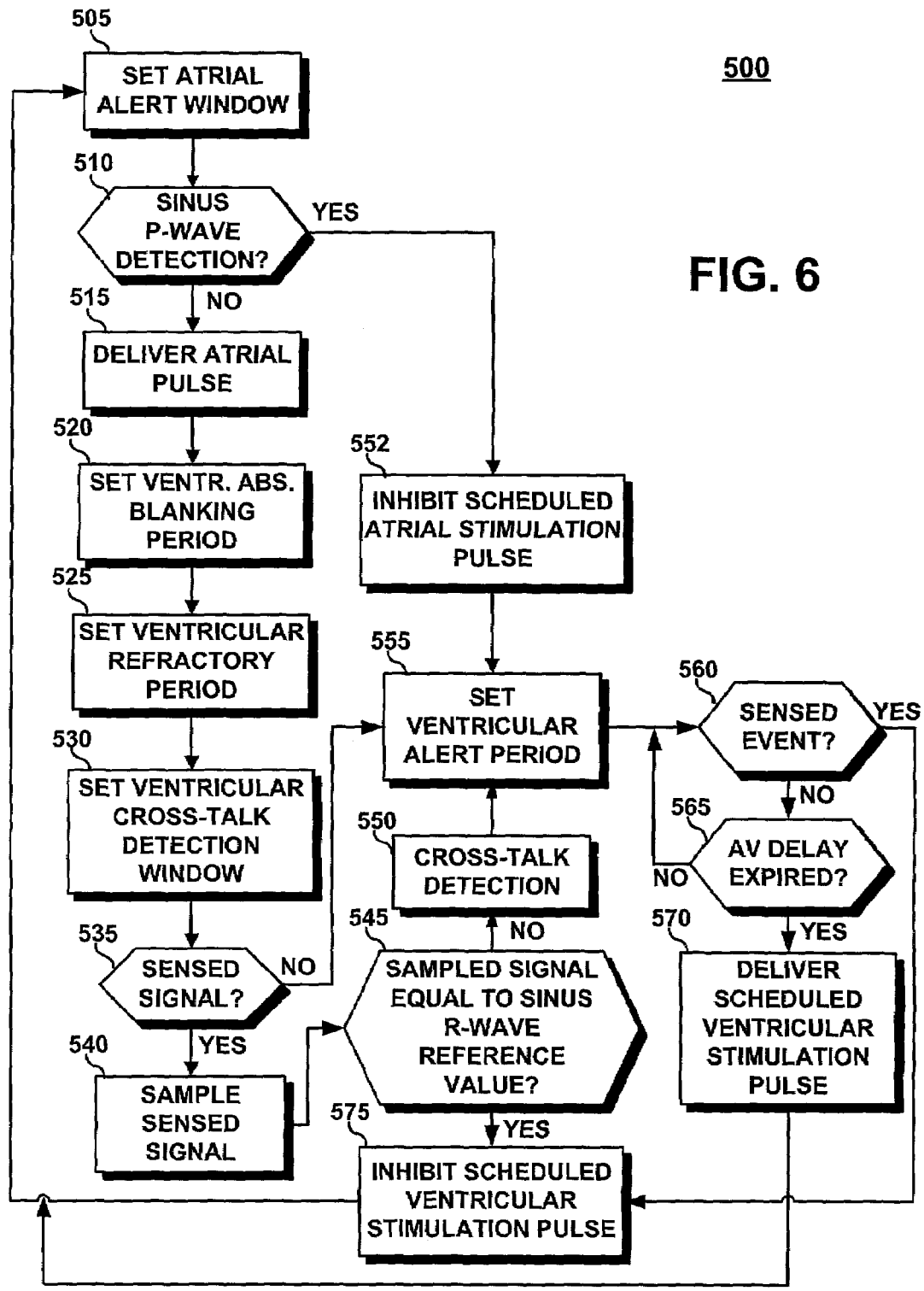
FIG. 6 is a flow chart depicting a method for discriminating between cross talk and intrinsic R-waves in a ventricular channel during dual chamber stimulation, according to the present invention.

In FIG. 6, method 500 provides an overview of operations included in one embodiment of the present invention for discriminating between cross talk and intrinsic R-waves in the ventricular channel during dual chamber stimulation. At step 505, microcontroller 60 initiates an atrial alert window for sensing intrinsic atrial events by the atrial sensing circuit 82.

At decision step 510, microcontroller 60 determines if a sinus P-wave has been detected. If a P-wave is detected, method 500 advances to step 552 wherein microcontroller 60 inhibits the scheduled atrial stimulation pulse. At step 555, a ventricular alert period is set for sensing for an intrinsic R-wave by the ventricular sensing circuit 84.

If a P-wave is not detected at step 510, an atrial stimulation pulse is delivered at the appropriate time interval by atrial pulse generator 70 at step 515. The atrial stimulation pulse is followed by an absolute ventricular blanking period set at step 520 and a ventricular refractory period set at step 525.

At step 530, a cross talk detection window is set following the ventricular refractory period. Microcontroller 60 determines if a ventricular signal is sensed during the cross talk detection window at decision step 535. If a ventricular signal is not sensed during the cross talk detection window, a ventricular alert period is set at step 555 to allow ventricular sensing circuit 84 to detect intrinsic R-waves.

If a ventricular signal is sensed during the cross talk detection window as determined at decision step 535, the signal is sampled at step 540 by data acquisition system 90 and a characteristic value is determined. The characteristic value of the sampled signal is compared to a sinus R-wave reference value at decision step 545 to determine if the sensed signal is a sinus R-wave.

If the sampled signal characteristic value is found to approximately equal the sinus R-wave reference value, the microcontroller 60 inhibits the scheduled ventricular stimulation pulse at step 575. The device 10 then returns to step 505 of method 500 to set the next atrial alert window for the next cardiac cycle.

If the sampled signal sensed during the cross talk detection window does not approximately equal the sinus R-wave reference value as determined at decision step 545, microcontroller 60 identifies the sensed signal as cross talk at step 550. The response of device 10 is to ignore the cross talk and set the next ventricular alert period at step 555 to continue sensing for an intrinsic R-wave.

If a sensed event is detected prior to the expiration of the AV delay, as determined at decision steps 560 and 565, respectively, the scheduled ventricular stimulation pulse is inhibited by the microcontroller 60 at step 575. If a ventricular event is not sensed during the ventricular alert period prior to expiration of the AV delay, the scheduled ventricular stimulation pulse is delivered at step 570. The method 500 then returns to step 505 to start the next atrial alert period for the next cardiac cycle.

Hence, the method 500 allows the device 10 to discriminate between cross talk and sinus R-waves sensed during the cross talk detection window and to appropriately withhold or deliver ventricular stimulation as needed. This method avoids delivering ventricular stimulation in response to sensed signals presumed to be cross talk only because they have occurred during the cross talk detection window.

Thus, a system and method have been described for distinguishing sensed sinus events from other non-sinus events and providing an appropriate device response to each type of event identified. While detailed descriptions of specific embodiments of the present invention have been provided, it would be apparent to those reasonably skilled in the art that numerous variations of the methods described herein are possible in which the concepts of the present invention may readily be applied. The descriptions provided herein are for the sake of illustration and are not intended to be exclusive.

What is claimed is:

1. A method of discriminating sinus events from non-sinus events using an implantable cardiac stimulation device, comprising:
   acquiring a reference signal value for a sinus event;
   acquiring a reference signal value for a non-sinus event;
   sampling a sensed signal resulting from an event in a cardiac chamber during a predetermined time period following an event in another cardiac chamber to obtain a characteristic signal value;
   identifying the sensed signal as a sinus event when the characteristic signal value substantially approximates the sinus-event reference signal value;
   identifying the sensed signal as a non-sinus event when the characteristic signal value substantially approximates the non-sinus-event reference signal value; and
   effecting operation of the implantable cardiac stimulation device in response to the identified sensed signal.

2. The method according to claim 1, further comprising setting the predetermined time period as an atrial refractory period and an atrial alert period following delivery of a ventricular stimulation pulse.

3. The method according to claim 2, wherein identifying the sensed signal as a sinus event comprises comparing a characteristic value of a signal sensed during any of the atrial refractory period or the atrial alert period to a reference signal value for a sinus P-wave.

4. The method according to claim 3, further comprising identifying the sensed signal as a sinus P-wave if the characteristic value of the sensed signal substantially matches a reference signal value for a sinus P-wave.

5. The method according to claim 4, wherein effecting operation of the implantable cardiac stimulation device in response to a detection of a sinus P-wave during the atrial refractory window comprises any of:
   inhibiting a scheduled atrial stimulation pulse;
   ignoring the P-wave for ventricular tracking purposes;
   automatic mode-switching;
   atrial rate determination for tachycardia detection; or
   atrial rate determination for dynamic atrial overdrive pacing.

6. The method according to claim 5, wherein effecting operation of the implantable cardiac stimulation device in response to a detection of a sinus P-wave during the atrial alert period comprises any of:
   inhibiting a scheduled atrial stimulation pulse;
   ventricular tracking of the P-wave;
   determining atrial rate for tachycardia detection; or
   determining atrial rate for dynamic atrial overdrive pacing.

7. The method according to claim 6, wherein, if the sensed signal does not substantially match the reference signal value for a sinus P-wave, identifying the sensed signal as a non-sinus event if the characteristic value of the sensed signal approximately matches the reference signal value for a non-sinus event; and
   providing a non-sinus event response.

8. The method according to claim 7, wherein, if the sensed signal is identified as an ectopic P-wave, the step of providing a non-sinus event response comprises any of:
   ventricular tracking of the ectopic P-wave;
   adjusting a P-V interval;
   ignoring the ectopic P-wave for ventricular tracking purposes; or
   adjusting a dynamic atrial overdrive pacing rate.

9. The method according to claim 7, wherein, if the sensed signal is identified as a far-field R-wave, the step of providing a non-sinus event response comprises any of:
   ignoring the far-field R-wave for determination of atrial rate;
   ignoring the far-field R-wave for ventricular tracking;
   adjusting an atrial sensitivity; or
   adjusting a ventricular stimulation output level.

10. The method according to claim 7, wherein, if the sensed signal is identified as a retrograde P-wave, the step of providing a non-sinus event response comprises any of:
  ignoring the retrograde P-wave for determination of atrial rate; or
  ignoring the retrograde P-wave for ventricular tracking.

11. The method according to claim 7, further comprising identifying the sensed signal as non-cardiac noise if the sensed signal does not approximately match predetermined reference signal values.

12. The method according to claim 7, further comprising storing the sensed signal for subsequent classification if the sensed signal is identified as noise.

13. The method according to claim 1, wherein identifying the sensed signal as an event corresponding to a reference signal value comprises identifying any one or more of the following events:
  a sinus P-wave;
  a sinus R-wave;
  an ectopic P-wave;
  a far-field R-wave; and
  a retrograde P-wave.

14. The method according to claim 13, wherein obtaining a characteristic signal value comprises obtaining a characteristic signal value from any one or more of:
  a signal morphology;
  a peak amplitude;
  a maximum slope;
  a signal width; and
  a signal integral.

15. The method according to claim 13, further comprising setting a ventricular blanking period, a ventricular refractory period, and a cross talk detection window, that successively follow a delivery of an atrial stimulation pulse.

16. The method according to claim 15, wherein comparing the characteristic value comprises comparing a characteristic value of a signal sensed during the cross talk detection window to a reference signal value for a sinus R-wave.

17. The method according to claim 16, further comprising:
  identifying the sensed signal as a sinus R-wave if the characteristic value of the sensed signal substantially matches the reference signal value for a sinus R-wave; and
  providing a sinus R-wave response.

18. The method according to claim 17, wherein providing a sinus R-wave response comprises inhibiting a scheduled ventricular stimulation pulse.

19. The method according to claim 17, wherein if the sensed signal is not identified as a sinus R-wave, identifying the sensed signal as cross talk; and
  providing a cross talk detection response.

20. The method according to claim 19, wherein providing the cross talk detection response comprises setting a ventricular alert period for sensing a sinus R-wave.

21. A cardiac stimulation device capable of discriminating sinus events from non-sinus events, comprising:
  a memory that stores a reference signal value for each of a sinus event and a non-sinus event;
  a sampler that samples a sensed signal resulting from an event in a cardiac chamber during a predetermined time period following an event in another cardiac chamber to obtain a characteristic signal value;
  a control circuit that identifies the sensed signal as a sinus event when the characteristic signal value substantially approximates the sinus-event reference signal value, identifies the sensed signal as a non-sinus event when the characteristic signal value substantially approximates the non-sinus-event reference signal value, and effects operation of the implantable cardiac stimulation device in response to the identified sensed signal.

22. The cardiac stimulation device according to claim 21, wherein the control circuit identifies a sensed signal as any one or more of the following events:
  a sinus P-wave;
  a sinus R-wave;
  an ectopic P-wave;
  a far-field R-wave; and
  a retrograde P-wave.

23. The cardiac stimulation device according to claim 22, wherein the sampler obtains the characteristic signal value from any one or more of:
  a signal morphology;
  a peak amplitude;
  a maximum slope;
  a signal width; and
  a signal integral.

24. The cardiac stimulation device according to claim 23, further comprising a timing circuit that sets the predetermined time period as an atrial refractory period and an atrial alert period following delivery of a ventricular stimulation pulse.

25. The cardiac stimulation device according to claim 24, further comprising a comparator that compares the characteristic value of a signal sensed during any of the atrial refractory period or the atrial alert period to a reference signal value for a sinus P-wave.

26. The cardiac stimulation device according to claim 25, wherein the control circuit identifies the sensed signal as a sinus P-wave if the characteristic value of the sensed signal substantially matches a reference signal value for a sinus P-wave.

27. The cardiac stimulation device according to claim 26, wherein, if the sensed signal does not substantially match the reference signal value for a sinus P-wave, the control circuit identifies the sensed signal as a non-sinus event if the characteristic value of the sensed signal approximately matches the reference signal value for a non-sinus event; and
  the pulse generator provides a non-sinus event response.

28. The cardiac stimulation device according to claim 26, wherein the control circuit identifies the sensed signal as non-cardiac noise if the sensed signal does not approximately match predetermined reference signal values.

29. The cardiac stimulation device according to claim 22, further comprising a timing circuit that sets a ventricular blanking period, a ventricular refractory period, and a cross talk detection window, that successively follow a delivery of an atrial stimulation pulse.

30. The cardiac stimulation device according to claim 29, wherein the comparator compares the characteristic value of a signal sensed during any the cross talk detection window to a reference signal value for a sinus R-wave.

31. An implantable cardiac stimulation device comprising:
  means for acquiring a reference signal value for each of a sinus event and a non-sinus event;
  means for detecting a cardiac event in a cardiac chamber during a predetermined time period following an event in another cardiac chamber and for obtaining a characteristic signal value of the cardiac event;
  means for identifying the cardiac event as a sinus event when the characteristic signal value substantially approximates the sinus-event reference signal value;

means for identifying the cardiac event as a non-sinus event when the characteristic signal value substantially approximates the non-sinus-event reference signal value; and means for effecting operation of the implantable cardiac stimulation device in response to the identified cardiac event.

32. The cardiac stimulation device according to claim 31, wherein the identifying means identifies a cardiac event as any one or more of the following events:
   a sinus P-wave;
   a sinus R-wave;
   an ectopic P-wave;
   a far-field R-wave; and
   a retrograde P-wave.

33. The cardiac stimulation device according to claim 32, wherein the sampling means obtains the characteristic signal value from any one or more of:
   a signal morphology;
   a peak amplitude;
   a maximum slope;
   a signal width; and
   a signal integral.

34. The cardiac stimulation device according to claim 31, further comprising:
   timing means for setting the predetermined time period as an atrial refractory period and an atrial alert period following delivery of a ventricular stimulation pulse; and
   comparing means for comparing the characteristic value of a signal sensed during any of the atrial refractory period or the atrial alert period to a reference signal value for a sinus P-wave.

35. The cardiac stimulation device according to claim 34, wherein the identifying means identifies the cardiac event as noise where the characteristic signal value does not approximately match a plurality of predetermined reference signal values.

36. The cardiac stimulation device according to claim 32, further comprising timing means for setting a ventricular blanking period, a ventricular refractory period, and a cross talk detection window, that successively follow a delivery of an atrial stimulation pulse; and
   wherein the comparing means compares the characteristic value sensed during the cross talk detection window to a reference signal value for a sinus R-wave.

37. A method of discriminating sinus events from non-sinus events using an implantable cardiac stimulation device, the method comprising:
   acquiring reference signal data for each of a predetermined sinus event and a predetermined non-sinus event;
   processing a sensed signal resulting from an event in a cardiac chamber during a predetermined time period following an event in another cardiac chamber to obtain sensed signal data;
   identifying the sensed signal as a predetermined sinus event when the sensed signal data substantially approximates the sinus-event reference signal data;
   identifying the sensed signal as a predetermined non-sinus event when the sensed signal data substantially approximates the non-sinus-event reference signal data; and
   effecting operation of the implantable cardiac stimulation device in response to the identified sensed signal.

* * * * *